(12) United States Patent
Freter et al.

(10) Patent No.: US 8,598,496 B2
(45) Date of Patent: Dec. 3, 2013

(54) METHOD FOR TESTING THE OPERATION OF A HEATING ELEMENT USED FOR AN ACTIVATED CARBON FILTER

(75) Inventors: Heiko Freter, Einbeck (DE); Tobias Lang, Gieboldehausen (DE)

(73) Assignee: A. Kayser Automotive Systems GmbH (DE)

( * ) Notice: Subject to any disclaimer, the term of this patent is extended or adjusted under 35 U.S.C. 154(b) by 1015 days.

(21) Appl. No.: 12/573,368

(22) Filed: Oct. 5, 2009

(65) Prior Publication Data
US 2011/0080159 A1    Apr. 7, 2011

(51) Int. Cl.
*H05B 3/02* (2006.01)
*G01R 31/08* (2006.01)
*G01R 27/08* (2006.01)
*G01R 31/00* (2006.01)
*G01R 25/00* (2006.01)
*H03D 13/00* (2006.01)

(52) U.S. Cl.
USPC ...... 219/483; 324/522; 324/713; 324/750.01; 324/76.77

(58) Field of Classification Search
USPC ........... 219/483; 324/522, 713, 750.01, 76.77
See application file for complete search history.

(56) References Cited

U.S. PATENT DOCUMENTS

| | | | | |
|---|---|---|---|---|
| 5,075,537 A * | 12/1991 | Lorenzen et al. | ............. | 219/497 |
| 5,245,693 A * | 9/1993 | Ford et al. | ............. | 392/470 |
| 5,770,836 A * | 6/1998 | Weiss | ............. | 219/481 |
| 6,199,397 B1 * | 3/2001 | Khelifa et al. | ............. | 62/317 |
| 6,276,202 B1 * | 8/2001 | Latarius | ............. | 73/335.05 |
| 2009/0320805 A1 * | 12/2009 | Lang et al. | ............. | 123/518 |

* cited by examiner

*Primary Examiner* — J. H. Hur
(74) *Attorney, Agent, or Firm* — Fox Rothschild LLP

(57) ABSTRACT

The invention relates to a method for testing the operation of an electric heating element which is used for heating activated carbon of an activated carbon filter and/or air which is guided through the activated carbon for the regeneration thereof. The heating element has a PTC-characteristic (positive temperature coefficient characteristic). The strength of a current flow through the heating element in a heating phase selected for the operational testing is measured at a point in time or over a time period and is used for the operational testing, in that at least one measured current flow value is compared with a corresponding current flow value to be anticipated during defect-free operation of the heating element, and the heating element is considered to be defective in the event of a deviation which exceeds a predetermined measurement.

7 Claims, 2 Drawing Sheets

METHOD FOR TESTING THE OPERATION OF A HEATING ELEMENT USED FOR AN ACTIVATED CARBON FILTER

BACKGROUND OF THE INVENTION

The invention relates to a method for testing the operation of an electric heating element which is used for heating activated carbon of an activated carbon filter and/or air which is guided through the activated carbon for the regeneration thereof. In the case of one of the methods, the heating element itself has a PTC-characteristic (positive temperature coefficient characteristic). In the case of two further methods, an electric resistor which is electrically connected to the heating element has a PTC-characteristic. The resistor is a barretter and is designated hereinafter as a PTC-resistor.

When using a hybrid drive for a motor vehicle, which drive is characterized by an internal combustion engine and an electric motor, the time during which the internal combustion engine is in operation is reduced by the time during which the electric motor is operated. This situation is significant inter alia also for an activated carbon filter which is connected to a fuel tank serving to supply the internal combustion engine, as a regeneration of the activated carbon filter is limited to the times of operation of the internal combustion engine.

In general, the fuel tank is connected via a line to the ambient atmosphere, via which a pressure build-up and similarly a negative pressure are prevented in the head space of the tank and can be adjusted during refueling, during the removal of fuel or as a result of a temperature-induced evaporation of fuel. An activated carbon filter which is typically disposed in this line is intended to prevent hydrocarbons from passing into the environment in this way.

This type of activated carbon filter consists generally of a container which is arranged to receive activated carbon particles and is designed with connections to establish a connection to the fuel tank, the ambient atmosphere and the intake line of the internal combustion engine.

In order to reduce the amount of activated carbon to be used, the connection which is connected to the said intake line serves during a flushing phase to guide ambient air through the activated carbon filling of the filter, wherein by means of desorption the air absorbs adsorptively bonded hydrocarbons and introduces them into the combustion chamber of the engine, so that as a result the activated carbon is regenerated. However, this procedure necessitates operation of the internal combustion engine. However, since the amount of hydrocarbons, which issue out of the head space of the tank as a result of evaporation and which are to be absorbed in the activated carbon filling, is independent of the operation time of the vehicle, in the case of a hybrid drive the regeneration procedure must be brought to a conclusion in a relatively short time.

It is generally known that the conditions of a regeneration in terms of an acceleration can be improved by the thermal conditions of this conversion, in that the air used for regeneration and/or the activated carbon are heated.

An activated carbon filter of this type, whose activated carbon filling can be heated, is known from the German patent application 10 2009 020 703.1, the content of which is to be hereby incorporated by reference. In this case, electrically operated heating elements having a PTC-characteristic are used, so that in a convenient manner heating of the regeneration air stream or the activated carbon is ensured. For reasons of explosion-protection, the maximum temperature of the regeneration air stream and the activated carbon must be limited. To this end, a heating element having a PTC-characteristic is advantageously used which is heated as a result of an electric current flow and thus serves as a heating element. At the same time, the electric resistance of the heating element increases as the temperature increases, whereby the electric current flow and thus the heating output are reduced. This gives rise to a self-regulating procedure which leads to a controlled temperature of this heating element. The maximum temperature is set by the chemical build-up of the PTC-heating element. The interdependency of the current flow, heating output and temperature can be expressed in the following formulae:

I—electric current
U—electric voltage (is generally constant in the application)
R—electric resistance
P—electric output (corresponds to the heating output)
Since $$I = U/R$$

the current flow is reduced when voltage is constant, if the resistance increases as a result of an increase in temperature.

$$P = U^2/R$$

If the resistance increases, the heating output is reduced when voltage is constant.

$$P = I^2 \times R$$

It is apparent from this that when voltage is constant the heating output is proportional to the square of the current consumption of an electric element having a PTC-characteristic. It can be assumed that voltage will be constant in the application in a passenger vehicle, since it can be presumed that in this case a uniform vehicle electric system voltage is provided. However, since the influence of the variable voltage upon the current flow and the output is also expressed in the formulae above, a variable voltage can also be taken into consideration by means of a voltage measurement.

A particular characteristic of the electric devices having a PTC-characteristic (referred to hereinafter as PTC-elements) is that at the beginning of the heating phase a high electric current flow always flows through the elements and is reduced after a short time. This behavior is virtually independent of the PTC-temperature during the beginning of the heating phase and of whether the element has air to be heated passing through it.

An On-Board-Diagnosis (OBD) law which demands monitoring of exhaust gas-relevant electric components has been in force in California since 1988. In 1994 this law was tightened in California by OBD II. Hereafter, all components which are used for monitoring emission-relevant components are also to be monitored. Since, as described above, heating of the air used for regeneration and/or the activated carbon is provided for specific vehicles and the heating has a significant influence upon the fuel emissions of the vehicle, it is necessary to monitor that the heating operates correctly.

SUMMARY OF THE INVENTION

The object of the invention is to provide a method, by means of which the operation of an electric heating element can be tested, wherein the heating element has a PTC-characteristic and is used for heating activated carbon of an activated carbon filter and/or air which is guided through the activated carbon for the regeneration thereof.

It is also the object of the invention to provide a method, by means of which the operation of an electric heating element can be tested, wherein the heating element is regulated in terms of its temperature by an electric resistor having a PTC-characteristic and is used for heating activated carbon of an activated carbon filter or air which is guided through the activated carbon for the regeneration thereof.

The first-named object is achieved by the features of the invention as described below. The method serves to test whether a heating element is operating without any defects. The heating element is used for heating activated carbon of an activated carbon filter or air which for flushing purposes is guided through the activated carbon for the regeneration thereof. The heating element can also be used in order to heat both the activated carbon and the air guided therethrough. The heating element is electrically operated and has itself a PTC-characteristic, as has been described above.

The strength of the current which flows through the heating element in a heating phase selected for the operational testing is measured at a point in time and/or over a specified time period and is used for the operational testing. This takes place in that at least one measured current flow value is compared with a corresponding current flow value which is to be anticipated during a defect-free operation of the heating element. The heating element is then considered to be defective if a deviation between the measured current flow values and the current flow values to be anticipated exceeds a predetermined measurement.

The above-described PTC-characteristic is used in accordance with the invention, whereby at the beginning of an electric current flow there is a high current flow value and the current flow then rapidly falls. Since this maximum value is characteristic of a specific design of the element having the PTC-characteristic, deviations from the PTC-characteristic indicate a defect in the heating or heating element. The current flow progression which decreases after a maximum is reached and which depends to a certain degree upon the temperature of the heating element at the beginning of the heating phase is also characteristic and can be used for defect-testing. The method in accordance with the invention is provided in particular for use in a passenger vehicle.

The method in accordance with the invention conveniently permits operational testing of the heating element. This testing which can also be defined as a part of a test cycle can take place if specifically no flushing of the activated carbon occurs as a result of regeneration air being guided therethrough. However, the testing can also be performed during a flushing phase.

In the above-described method, the heating element itself has the PTC-characteristic. This means that the electric resistance of the heating element increases as the temperature increases, whereby the current flow through the heating element is reduced and the heating output is reduced accordingly.

The second-named object is achieved by the additional features of the invention described below. This method corresponds to the above-described method but with the difference that an electric resistor which is not the heating element has a PTC-characteristic and the PTC-resistor is electrically connected to the heating element such that the current flowing through the heating element also flows through the PTC-resistor. The PTC-resistor is disposed in spatial terms adjacent to the heating element in such a manner that the heating element also heats the PTC-resistor. This heating can be effected in particular by the radiation of heat from the heating element. The PTC-resistor serves as a control element for the heating element. In specific terms, this means that if by reason of the heating of the PTC-resistor its electric resistance value increases and therefore the current flowing through the PTC-resistor is reduced, the heating output of the heating element also decreases.

Although in this method the PTC-resistor has the PTC-characteristic, i.e. its electric resistance increases as the temperature increases, so that at constant voltage the current flow through the PTC-resistor decreases, it will generally be the case that the PTC-resistor heats up of its own accord only to a relatively small extent as current increases, so that it is important that the heating starts from the heating element. However, in essence it can also be provided that the PTC-resistor is configured in such a manner that it heats itself up to a sufficient extent as current increases, in order to achieve the desired control effect.

The advantages described in connection with the first-named method also apply to the second-named method in accordance with the invention.

The second-named object is also achieved by still further features of the invention described below. This method corresponds to the second above-described method, but with the difference that in any event the heating element serves to heat an air flow provided for the regeneration of the activated carbon and the PTC-resistor is disposed in a spatial relationship with respect to the heating element such that the PTC-resistor is heated by virtue of the fact that the regeneration air flow heats the PTC-resistor. In this case, the PTC-resistor is also used as the control element for the heating element. However, in this method the required air flow only permits operational testing of the heating element during a flushing phase, provided that no heat is transferred from the heating element to the PTC-resistor without a regeneration air flow. The reason for this is that it is also fundamentally possible both for the PTC-resistor to be heated by an existing regeneration air flow and for heat to be transferred directly in this way.

The advantages described in connection with the first-named method also apply to the third-named method in accordance with the invention. In the third-named method, the heating element can additionally be used to heat the activated carbon.

In principle, the methods in accordance with the invention for operational testing or monitoring are possible irrespective of whether a single or several electrically interconnected heating elements are being taken into account.

The following embodiments relate to all three above-described methods in accordance with the invention.

Preferably, a stated time period, during which the current flow is measured, is selected such that it includes the beginning of the heating phase selected for the operational testing.

In particular, the time period can be selected such that the absolute maximum current flow value to be anticipated during defect-free operation of the heating element is within the time period. It is a significant advantage of the selection of such a time period provided for the operational testing that the rapid increase of the strength of current to a maximum value falls within this period and this maximum strength of current value depends only to a slight extent upon the temperature of the heating element or the PTC-resistor at the beginning of the heating phase. This starting temperature of the heating element or the PTC-resistor can be different by reason of different ambient temperatures or even by reason of the fact that possibly shortly beforehand a regular flushing phase—which is not performed for the test—has taken place. During this type of flushing phase, the temperature of the heating element rises approximately to 150° C. By reason of this very incisive characteristic of the absolute maximum strength of current, a defect-free operation of the heating element can be detected fairly reliably in the case of this embodiment. The reason for this is that the range of fluctuation of the absolute maximum strength of current which is caused by different starting temperatures of the heating element is relatively narrow.

Therefore, in a preferred manner the maximum value of the current flow is determined within this initial time period by measurement and the heating element is considered to be defective if the maximum current flow value is outside a range of fluctuation which has been previously established in dependence upon different possible starting temperatures of the heating element or PTC-resistor. The predetermined measurement stated above is thus based upon this range of fluctuation which could also be defined as a tolerance range, which also applies accordingly to the ranges of fluctuation stated hereinafter.

The said initial time period can amount approximately to 50 seconds. The range of fluctuation provided can be 11 to 13 amps.

In addition or even as an alternative to the above initial time period, a time period can be provided for the operational testing which in terms of time begins subsequently in the heating phase selected for the operational testing. This subsequent specified time period is generally such that it does not include the above-described maximum current flow value which is related to the entire heating phase. However, in this subsequent time period, the dependence of the strength of current upon the starting temperature of the heating element is such that under certain circumstances the (relative) maximum current flow value present within this time period can vary to a greater extent than the absolute maximum current flow value during the initial time period.

It can be provided that the heating phase selected for the operational testing is selected such that it does not overlap with a flushing phase. Then, the heating phase is thus only initiated for the operational testing. In this case, it can be provided that the heating element is then considered to be defective if a current flow value which is used for the testing and is measured within this subsequent time period is outside a range of fluctuation which has been previously determined in dependence upon different possible starting temperatures of the heating element or PTC-resistor.

In the event that a flushing phase actually takes place during the provided operational testing, i.e. regeneration air is guided through the activated carbon, the heating element can be considered to be defective if the following occurs: a current flow value which is used for the testing and is measured within the subsequent time period is outside a range of fluctuation which has been determined in dependence upon the strength and temperature of the regeneration air flow guided through the activated carbon, and upon different possible starting temperatures of the heating element or PTC-resistor. By reason of the regeneration air flow which is present, the strength of current values fluctuate to a greater extent during defect-free operation of the heating element than when the air flow is not present.

Provision can be made to use all current flow values, which are measured within the subsequent time period, for the purpose of testing the operation of the heating element. However, it would also be possible to examine only a relative maximum current flow value or a minimum current flow value to verify whether it is within the range of fluctuation.

The range of fluctuation can have a constant upper and lower limit value. However, it is also possible to provide the range of fluctuation with upper and lower limit values which vary over the time period whilst adapting to the current flow values to be anticipated during defect-free operation of the heating element. In other words, the range of fluctuation is then limited by an upper limit curve and a lower limit curve which quasi envelop the current flow values to be anticipated.

The subsequent time period is preferably selected in such a manner that the strength of current value to be anticipated is close to an asymptotically approximated end value within this time period because then the fluctuation of the strength of current which is caused by the different starting temperatures of the heating element or PTC-resistor is relatively low. In this case, this time period is thus approximately towards the end of the heating phase.

The subsequent time period can be e.g. 180 to 200 seconds after the beginning of the heating phase.

In addition to or even as an alternative to the above initial or subsequent time period, merely one point in time can be provided for the operational testing which in terms of time occurs subsequently in the heating phase which is selected for the operational testing. If during the heating phase provided for testing no regeneration air is guided through the activated carbon, it can be provided that the heating element is then considered to be defective if the current flow value at the point in time is outside a range of fluctuation which has been previously determined in dependence upon different possible starting temperatures of the heating element or PTC-resistor. In the case of regeneration air which is present during the said heating phase, it can be provided that the heating element is then considered to be defective if the current flow value at the point in time is outside a range of fluctuation which has been previously determined in dependence upon the strength and temperature of the regeneration air flow guided through the activated carbon, and upon different possible starting temperatures of the heating element or PTC-resistor.

The range of fluctuation provided can be e.g. 2 to 4 amps, in particular if the heating phase selected for the operational testing does not overlap with a flushing phase. The current flow values to be anticipated and thus the ranges of fluctuation are generally different depending upon whether or not a flushing phase takes during testing. The ranges of fluctuation are generally established in a phase of component testing.

If the absolute maximum current flow value measured in the initial time period or even the relative maximum current flow value measured in the subsequent time period are too low, this can be caused by a defect in the form of a broken cable or a destroyed heating element or PTC-resistor. In the event that a current flow is too high, e.g. an electric short-circuit can be provided.

If the operational testing takes place during an existing regeneration air flow, a blockage in the air channels provided for heating purposes can also be found to be a possible defect. In the case of the two first-named methods in accordance with the invention, a current flow which is too low occurs in this case as the heating energy cannot be dissipated.

The determination of the range of fluctuation in dependence upon different possible starting temperatures of the heating element or PTC-resistor, as described above in each case, is to be understood to mean that the respective range of fluctuation is determined overall for the different possible starting temperatures and not in each case for merely one of the possible starting temperatures. In addition, the above-described ranges of fluctuation can also be determined in dependence upon ageing of the heating element.

It should be ensured that the beginning or the end of a regular flushing phase does not fall within a time period provided for operational testing.

BRIEF DESCRIPTION OF THE DRAWINGS

The invention will be described in more detail hereinafter with reference to exemplified embodiments, wherein reference is made to the Figures, in which.

DETAILED DESCRIPTION OF THE INVENTION

Figure 1:
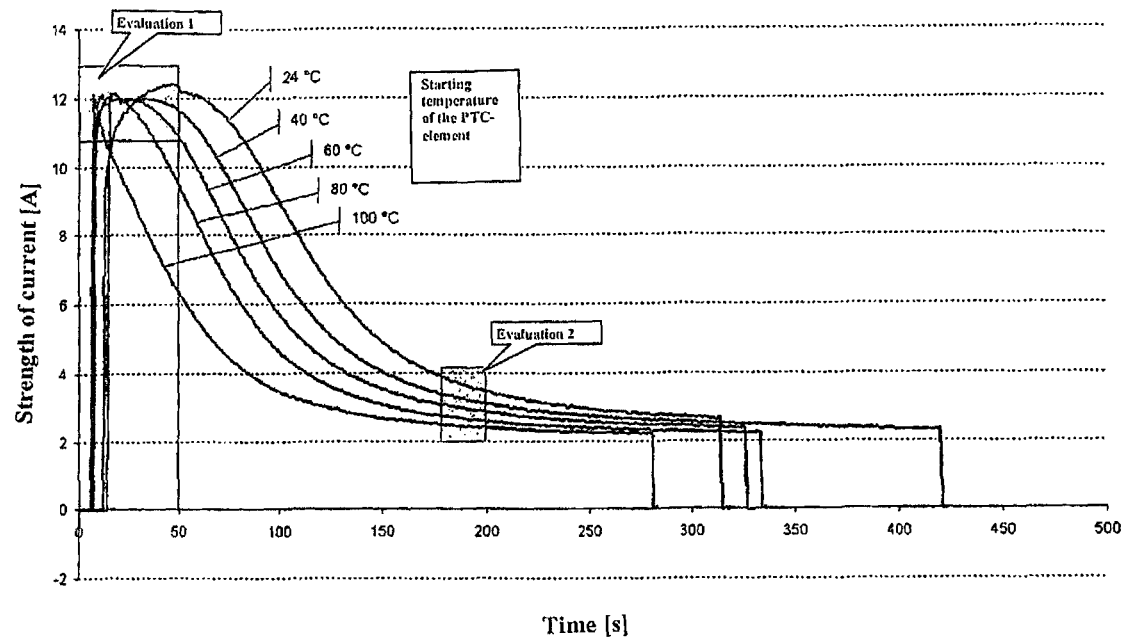
FIG. 1 shows a graph including the electric current consumption to be anticipated for a PTC-element, which is a heating element having a PTC-characteristic or a PTC-resistor, during inventive operational testing of a heating element without the simultaneous presence of a regeneration air flow.

FIG. 1 illustrates a total of five different measured current consumption curves which are produced at different starting temperatures of the PTC-element, namely 24, 40, 60, 80 and 100° C. These temperatures are identical to the starting temperature of the heating element used, if the PTC-element itself heats up, i.e. the PTC-element is a heating element having a PTC-characteristic. If the PTC-element is a PTC-resistor, the temperatures are possibly slightly lower than the respective starting temperature of the heating element, as the temperature of the PTC-resistor is produced—as described above—from a transfer of heat from the heating element. The progression of the current consumption is illustrated over time, wherein the strength of current goes to zero upon termination of the heating phase provided for the operational testing.

It is apparent that in each case at the beginning of the heating phase a considerable current peak, i.e. an absolute maximum current flow value, is achieved, wherein the strength of current falls rapidly after the current peak. It is also apparent that towards the end of the heating phase the strength of current asymptotically approximates an end value, wherein the variation of the strength of current becomes ever smaller in dependence upon the different starting temperatures. Towards the end of the heating phase, it can be said that to a certain extent the strength of current is "independent" of the starting temperature of the PTC-element.

FIG. 1 illustrates an initial time period which is defined as "Evaluation 1", and a subsequent time period which is defined as "Evaluation 2". Both time periods are used for testing the operation of the heating element. The initial time period begins shortly before current flows through the heating element, and extends over a period of time of ca. 50 seconds. During the initial time period, all five of the current consumption curves reach their absolute maximum value. It is provided that the heating element is then considered to be defective if this maximum value is not within the marked range of fluctuation of ca. 10.8 to 13 amps. It is also provided that the heating element is also considered to be defective if one of the strength of current values measured within the subsequent time period is outside the marked range of fluctuation of ca. 2.0 to 4.1 amps. It is evident that the permissible range of fluctuation could also be selected to be smaller if the subsequent time period was scheduled closer to the end of the respective heating phase. However, it can be assumed that the strength of current values can be reliably reproduced during defect-free operation of the heating element. The subsequent time period could thus also be reduced to a specific point in time, e.g. 190 seconds.

Figure 2:
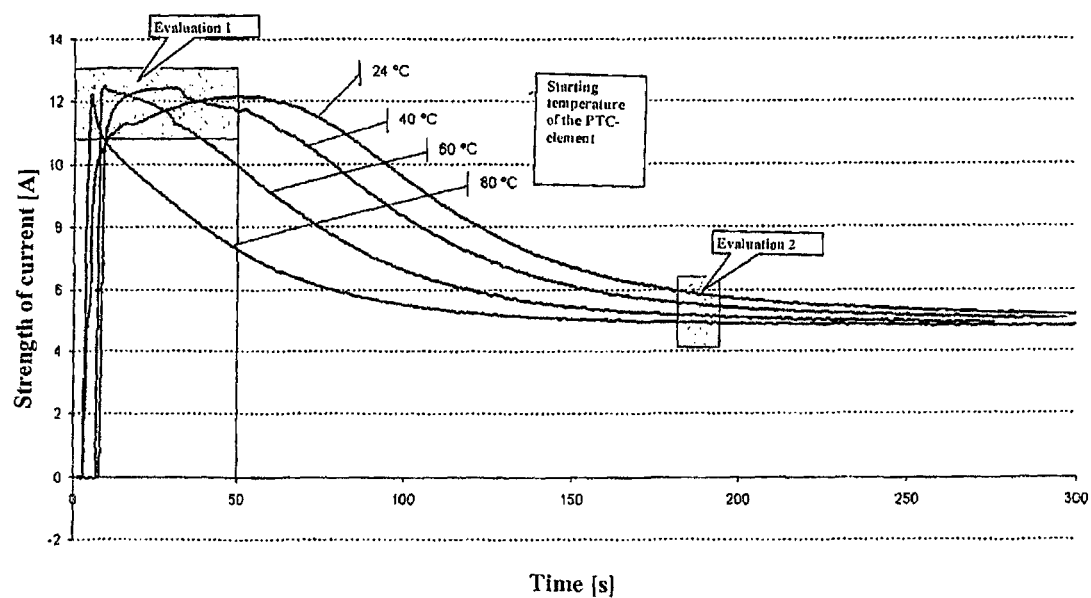
FIG. 2 shows a graph including the electric current consumption to be anticipated for a PTC-element, which is a heating element having a PTC-characteristic or a PTC-resistor, during inventive operational testing of a heating element with the simultaneous presence of a regeneration air flow.

FIG. 2 illustrates a total of four different measured current consumption curves which are produced at different starting temperatures of the PTC-element, namely 24, 40, 60 and 80° C. These temperatures are identical to the starting temperature of the heating element used, if the PTC-element itself heats up, i.e. the PTC-element is a heating element having a PTC-characteristic. If the PTC-element is a PTC-resistor the temperatures are possibly slightly lower than the respective starting temperature of the heating element, as the temperature of the PTC-resistor is produced—as described above—from a transfer of heat from the heating element, possibly by means of the regeneration air flow. The progression of the current consumption is again illustrated over time, wherein the end of the heating phase is not illustrated.

It is apparent that even in the case of this embodiment in accordance with the invention a considerable current peak, i.e. a maximum current flow value, is always achieved at the beginning of the heating phase, wherein after the current peak the strength of current falls slightly less rapidly than as shown in FIG. 1. It is also apparent that towards the end of the heating phase the strength of current approximates an end value, wherein the variation of the strength of current becomes ever smaller in dependence upon the different starting temperatures. Towards the end of the heating phase, it can also be said that to a certain extent the strength of current is "independent" of the starting temperature of the PTC-element.

FIG. 2 also illustrates an initial time period which is defined as "Evaluation 1" and a subsequent time period which is defined as "Evaluation 2". Both time periods are used for testing the operation of a heating element. The initial time period begins shortly before current flows through the heating element and extends over a time period of ca. 50 seconds. During the initial time period, all four of the current consumption curves reach their absolute maximum value. It is provided that the heating element is then considered to be defective if this maximum value is not within the marked range of fluctuation of ca. 10.8 to 13 amps. It is also provided that the heating element is then also considered to be defective if one of the strength of current values measured within the subsequent time period is outside the marked range of fluctuation of ca. 4.1 to 6.4 amps. In this case, the permissible range of fluctuation could also be selected to be smaller if the subsequent time period was scheduled closer to the end of the respective heating phase. Although the strength of current values to be anticipated during defect-free operation of the heating element depend not only upon the starting temperature of the PTC-element but also upon the regeneration air flow, it can also be assumed in this case that the strength of current values can be reliably reproduced during defect-free operation of the heating element. The subsequent time period could thus also be reduced to a specific point in time, e.g. 190 seconds.

Figure 3:
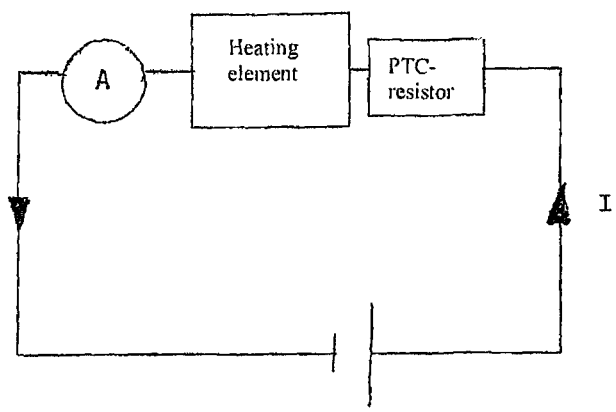
FIG. 3 shows a block diagram illustrating a heating element which is used according to a method in accordance with the invention and which for control purposes is connected to a PTC-resistor.

In accordance with FIG. 3, a PTC-resistor, a heating element for heating activated carbon of an activated carbon filter (not illustrated) and an ammeter which is designated by the letter "A" and is used to measure the strength of current I are connected in series. The heating elements is disposed adjacent to the PTC-resistor in such a manner that by means of heat transfer it generates substantially the same temperature in the PTC-resistor as it does in itself.

Figure 4:
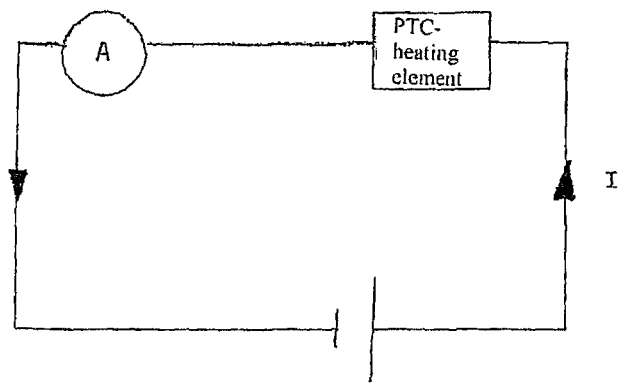
FIG. 4 shows a block diagram illustrating a heating element which is used according to a method in accordance with the invention and which itself has a PTC-characteristic.

In accordance with FIG. 4, a heating element for heating activated carbon of an activated carbon filter (not illustrated) and an ammeter which is designated by the letter "A" and is used to measure the strength of current I are connected in series. In contrast to the heating element as shown in FIG. 3, the heating element itself has a PTC-characteristic and is therefore defined as a PTC-heating element.

The invention claimed is:

1. Method for testing the operation of an electric heating element which is used for heating activated carbon of an activated carbon filter and/or air which is guided through the activated carbon for the regeneration thereof, wherein the heating element has a PTC-characteristic (positive temperature coefficient characteristic), and wherein the strength of a current flow through the heating element in a heating phase selected for the operational testing is measured at a point in time or over a time period and is used for the operational testing, in that at least one measured current flow value is compared with a corresponding current flow value to be anticipated during defect-free operation of the heating element, and the heating element is considered to be defective in the event of a deviation which exceeds a predetermined measurement, and wherein as the said time period, a time period is selected such that it begins in the beginning of the said heating phase or in a delayed manner in terms of time with respect to the beginning of the said heating phase, and wherein, if during the said heating phase no regeneration air is guided through the activated carbon, the heating element is considered to be defective if a current flow value which is used for the testing and is measured within the time period is outside a range of fluctuation which has been previously determined in dependence upon different possible starting temperatures of the heating element or of a PTC-resistor.

2. Method for testing the operation of an electric heating element which is used for heating activated carbon of an activated carbon filter and/or air which is guided through the activated carbon for the regeneration thereof, wherein the heating element has a PTC-characteristic (positive temperature coefficient characteristic), and wherein the strength of a current flow through the heating element in a heating phase selected for the operational testing is measured at a point in time or over a time period and is used for the operational testing, in that at least one measured current flow value is compared with a corresponding current flow value to be anticipated during defect-free operation of the heating element, and the heating element is considered to be defective in the event of a deviation which exceeds a predetermined measurement, and wherein as the said time period, a time period is selected such that it begins in a delayed manner in terms of time with respect to the beginning of the said heating phase, and wherein in the event of regeneration air being guided through the activated carbon during the said heating phase, the heating element is considered to be defective if a current flow value which is used for the testing and is measured within the time period is outside a range of fluctuation which has been previously determined in dependence upon the strength and temperature of the regeneration air flow guided through the activated carbon, and upon different possible starting temperatures of the heating element or of a PTC-resistor.

3. Method as claimed in claim 1, wherein all current flow values within the time period are used for the testing.

4. Method as claimed in claim 1, wherein the range of fluctuation varies over the time period in relation to an upper and a lower limit value for the range of fluctuation whilst adapting to the current flow values to be anticipated during defect-free operation of the heating element.

5. Method as claimed in claim 1, wherein the time period is 180 to 200 seconds after the beginning of the said heating phase.

6. Method for testing the operation of an electric heating element which is used for heating activated carbon of an activated carbon filter and/or air which is guided through the activated carbon for the regeneration thereof, wherein the heating element has a PTC-characteristic (positive temperature coefficient characteristic), and wherein the strength of a current flow through the heating element in a heating phase selected for the operational testing is measured at a point in time or over a time period and is used for the operational testing, in that at least one measured current flow value is compared with a corresponding current flow value to be anticipated during defect-free operation of the heating element, and the heating element is considered to be defective in the event of a deviation which exceeds a predetermined measurement, and wherein as the said point in time, a point in time is selected such that it is delayed in terms of time with respect to the beginning of the said heating phase, and wherein, if during the said heating phase no regeneration air is guided through the activated carbon, the heating element is considered to be defective if the measured current flow value at the point in time is outside a range of fluctuation which has been previously determined in dependence upon different possible starting temperatures of the heating element or of a PTC-resistor.

7. Method for testing the operation of an electric heating element which is used for heating activated carbon of an activated carbon filter and/or air which is guided through the activated carbon for the regeneration thereof, wherein the heating element has a PTC-characteristic (positive temperature coefficient characteristic), and wherein the strength of a current flow through the heating element in a heating phase selected for the operational testing is measured at a point in time or over a time period and is used for the operational testing, in that at least one measured current flow value is compared with a corresponding current flow value to be anticipated during defect-free operation of the heating element, and the heating element is considered to be defective in the event of a deviation which exceeds a predetermined measurement, and wherein as the said point in time, a point in time is selected such that it is delayed in terms of time with respect to the beginning of the said heating phase, and wherein in the event of regeneration air being guided through the activated carbon during the said heating phase, the heating element is considered to be defective if the measured current flow value at the point in time is outside a range of fluctuation which has been previously determined in dependence upon strength and temperature of the regeneration air flow guided through the activated carbon, and upon different possible starting temperatures of the heating element or of a PTC-resistor.

* * * * *